United States Patent [19]

Tröster

[11] Patent Number: 5,319,083
[45] Date of Patent: Jun. 7, 1994

[54] BLACK PERYENE-3,4,9,10-TETRACARBOXYLIC DIIMIDES, THEIR PREPARATION AND USE

[75] Inventor: Helmut Tröster, Königstein/Taunus, Fed. Rep. of Germany

[73] Assignee: Hoechst Aktiengesellschaft, Frankfurt, Fed. Rep. of Germany

[21] Appl. No.: 996,844

[22] Filed: Dec. 16, 1992

Related U.S. Application Data

[63] Continuation of Ser. No. 785,450, Oct. 31, 1991, abandoned.

[30] Foreign Application Priority Data

Nov. 3, 1990 [DE] Fed. Rep. of Germany .... P4035009

[51] Int. Cl.$^5$ ................................................ C09B 5/62
[52] U.S. Cl. ............................................................ 546/37
[58] Field of Search ........................................ 546/37

[56] References Cited

U.S. PATENT DOCUMENTS

| | | | |
|---|---|---|---|
| 3,615,800 | 10/1971 | Spietschka et al. | 106/228 Q |
| 4,450,273 | 5/1984 | Graser | 546/37 |
| 4,599,408 | 7/1986 | Spietschka et al. | 544/125 |
| 4,709,029 | 11/1987 | Spietschka et al. | 544/125 |
| 4,725,690 | 2/1988 | Graser | 546/37 |
| 4,831,140 | 5/1989 | Spietschka et al. | 546/37 |
| 4,845,223 | 7/1989 | Seybold et al. | 546/37 |

FOREIGN PATENT DOCUMENTS

| | | |
|---|---|---|
| PS0039482 | 4/1981 | European Pat. Off. . |
| PA0056870 | 5/1981 | European Pat. Off. . |
| PS2451780 | 10/1974 | Fed. Rep. of Germany . |
| AS2451781 | 1/1976 | Fed. Rep. of Germany . |
| PS2451783 | 9/1976 | Fed. Rep. of Germany . |
| OS3422757 | 1/1986 | Fed. Rep. of Germany . |
| OS3620659 | 1/1987 | Fed. Rep. of Germany . |
| PS1523475 | 12/1978 | United Kingdom . |
| PS1537358 | 12/1978 | United Kingdom . |
| PS2177103 | 1/1987 | United Kingdom . |

OTHER PUBLICATIONS

Y. Nagao et al., Dyes and Pigments, vol. 5, (1984), S. 171 ff.

Nagoa et al., Dyes & Pigments, vol. 6, (1985), S. 304 ff.

Primary Examiner—Marianne M. Cintins
Assistant Examiner—Catherine Scalzo
Attorney, Agent, or Firm—Connolly and Hutz

[57] ABSTRACT

The invention relates to perylene-3,4,9,10-tetracarboxylic diimides of the formula (I)

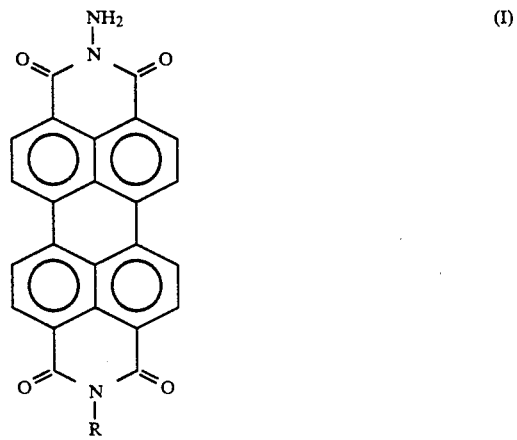

in which R is a 3'- and/or 4'-methoxybenzyl radical, and their preparation and use as black pigments, inter alia in paint preparations, printing inks or for the dyeing of polymers.

4 Claims, 2 Drawing Sheets

BLACK PERYENE-3,4,9,10-TETRACARBOXYLIC DIIMIDES, THEIR PREPARATION AND USE

This application is a continuation of application Ser. No. 07/785,450 filed on Oct. 31, 1991 abandoned.

Of the large number of perylenetetracarboxylic diimide colorants, only few compounds have been disclosed which have a black color and can be used as black pigments. They are described in German Offenlegungsschrift 2,451,780, GB-A 1,523,415, GB-A 1,537,358, DE-A 3,422,757 and GB-A 2,177,103 and in U.S. Pat. No. 4,450,273. These are exclusively symmetrically N,N'-substituted perylenetetracarboxylic diimides. The small number of such specific pigments can be explained by particular structural requirements which the dye molecule must fulfill in order to enable an arrangement of the molecules in the crystal lattice which results in a black color impression.

Most recently, many unsymmetrically N,N'-substituted perylenetetracarboxylic diimides have also been disclosed in the literature [Y. Nagao et al., Dyes and Pigments 5 (1984), 179–181, Tab. 3; likewise 6 (1985), 309, Tab. 3]. However, they do not include a black pigment.

The invention now relates to perylene-3,4,9,10-tetracarboxylic diimides of the formula (I) according to claim 1, and to their preparation and their use as black pigments.

As discussed in GB-A 2,177,103 cited above, a given molecular structure does not allow the expected color of the pigment to be predicted. Thus, in the case of the diimides according to the invention, it was not foreseeable that it would be possible to find black pigments even with an unsymmetrical molecular structure.

The new, asymmetrical perylenetetracarboxylic diimides (I) are highly suitable as black pigments for solvent- or water-based paints and printing inks and also for polymers, such as, for example, polyvinyl chloride and polyethylene.

The deep black or in a blend with, for example, white pigments gray shades obtained therewith are distinguished by very good general fastness properties, in particular excellent light and weather fastness. Owing to the diffuse reflection values in the red and near-infra red spectral region, which are very similar to those of chlorophyll, the pigments can also be used in particular in the preparation of camouflage paints. Compared with the black pigments from U.S. Pat. No. 4,450,273, they are distinguished in particular by a higher color strength.

To prepare the compounds of the formula (I), perylene-3,4,9,10-tetracarboxylic monoimides of the formula (II)

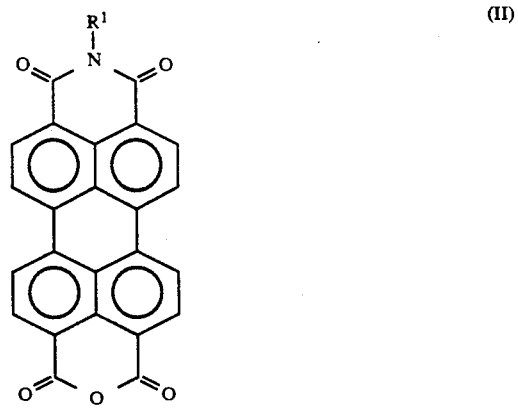

are condensed in a manner known per se with amines of the formula (III)

$$R^2—NH_2 \qquad (III).$$

$R^1$ and $R^2$ in these formulae have the following meaning: if $R^1$ in formula (II) is an amino group, $R^2$ in formula (III) is a 3- and/or 4-methoxybenzyl radical and vice versa.

The reaction can be carried out in water and/or organic solvents, such as methylglycol, glycol or quinoline at elevated temperature, in general at temperatures from 100° to 250° C., preferably from 120° to 200° C. at atmospheric pressure or, if desired, also at elevated pressure.

The compound (III) is used at least in equimolar amounts, but preferably in an excess of 20 to 100 mol %. The reaction product isolated in the usual manner can, if desired, be converted into the desired pigment form by suitable, customary finishing methods, such as milling, for example according to U.S. Pat. No. 3,615,800, or reprecipitation from sulfuric acid, followed, if desired, by a solvent treatment.

The monoimides of the formula (II) required as starting compounds can be prepared, for example, by the process described in U.S. Pat. No. 4,599,408, herein incorporated by reference, by reacting the corresponding perylene-3,4,9,10-tetracarboxylic monoanhydride monoalkali metal salts with compounds $R^1$—$NH_2$, in which $R^1$ has either the meaning of R or is an amino group.

Figure 1:
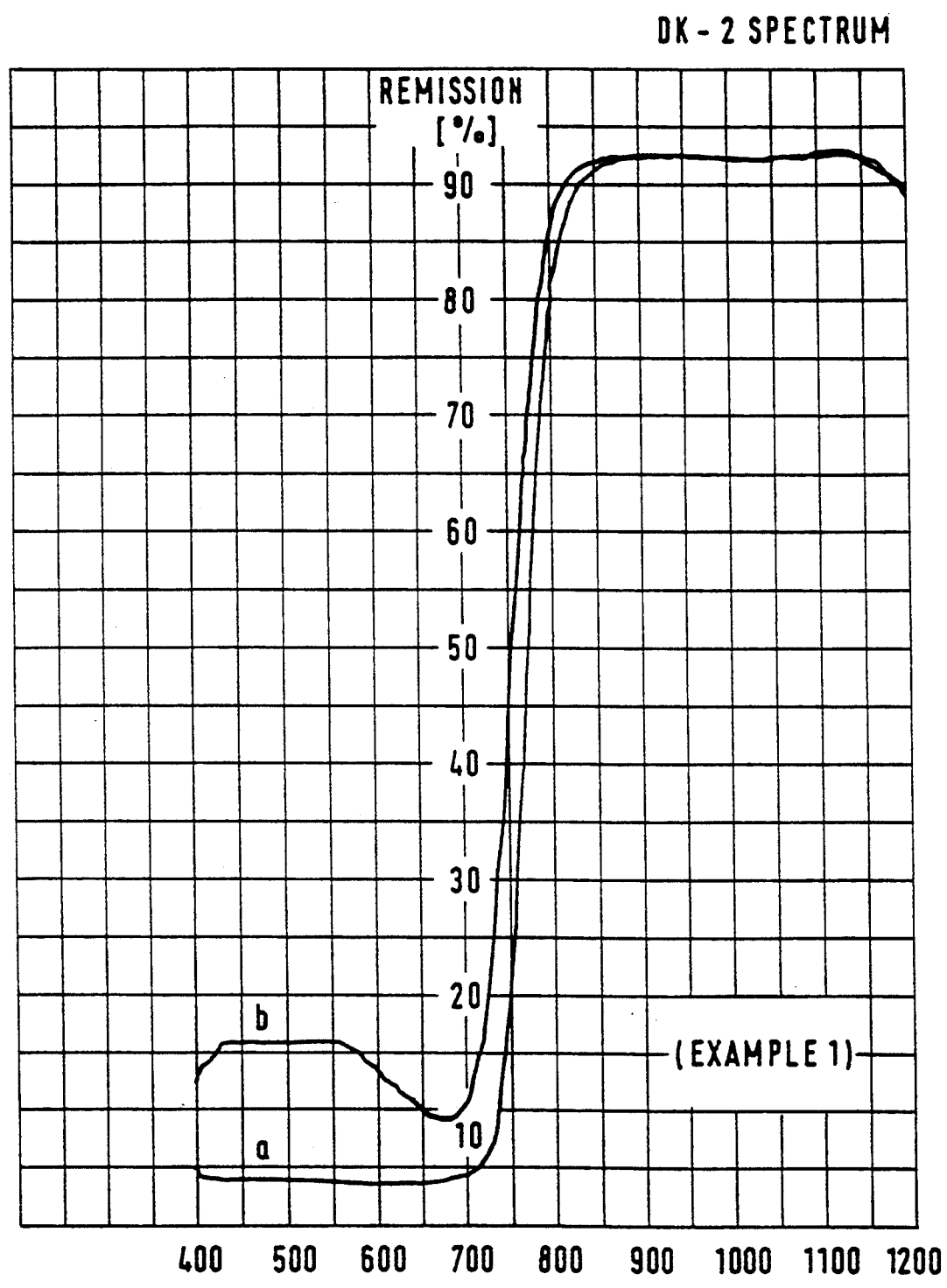
FIGS. 1 and 2 show reflection curves of coatings produced.
Figure 2:
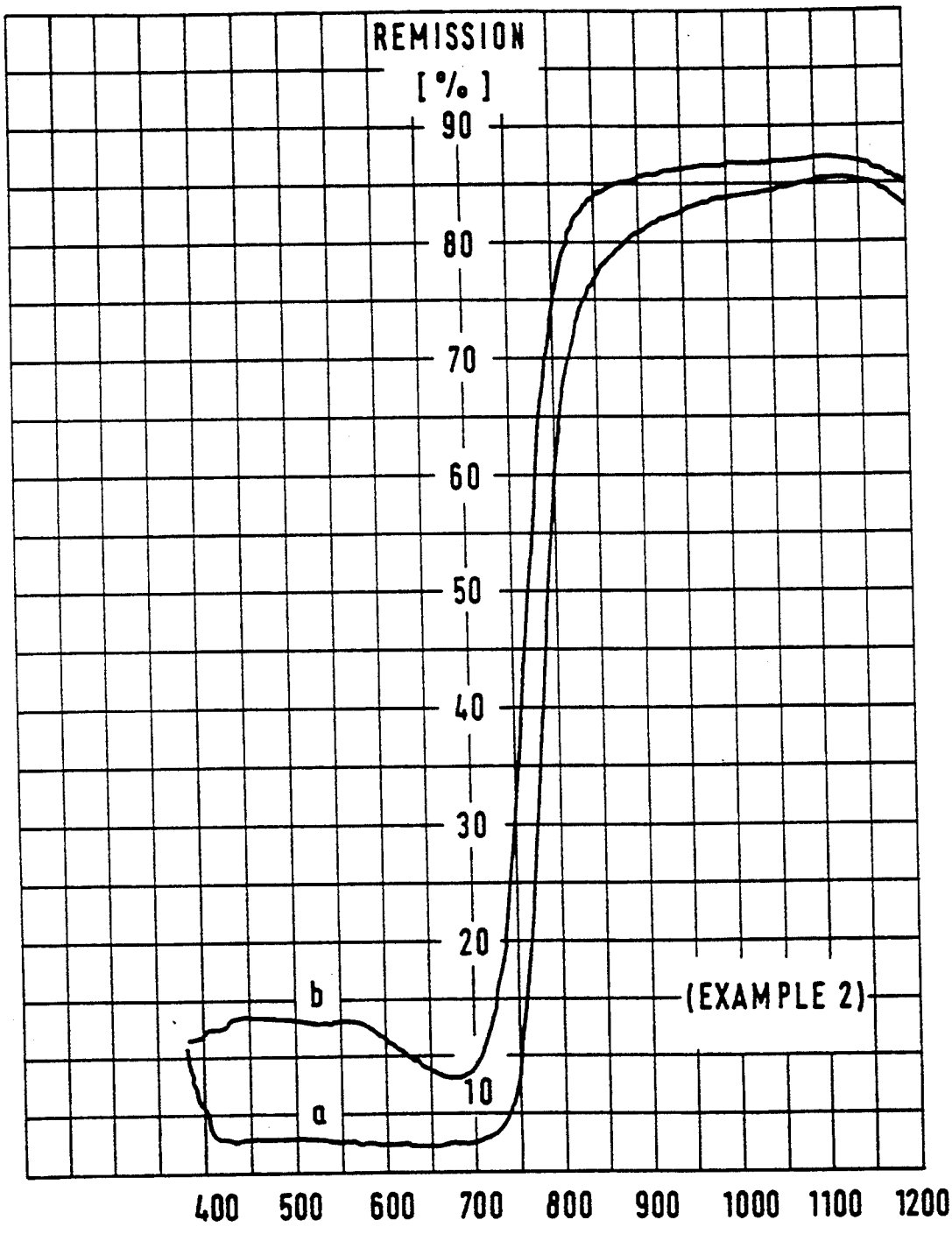

The invention is illustrated in more detail by way of the examples which follow.

I. Preparation Examples

1. Preparation of the Compound According to the Formula

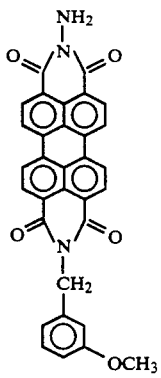

8.5 g of dihydrazinium sulfate (95% pure) were introduced into a solution of 200 ml of methylglycol and 100 ml of water, and 10.8 g of 50% potassium hydroxide solution were then poured in. 15.3 g of perylene-3,4,9,10-tetracarboxylic mono-3'-methoxybenzylimide were added to this mixture and reacted in an autoclave at 130°–140° C. for 3 hours.

The reaction product was filtered off with suction at room temperature, washed with methylglycol/water 1:1 until the filtrate run-off was colorless and finally washed with water and dried. 15.6 g (99.0% of theory) of the target product were obtained in the form of black crystals having a greenish surface luster.

Analysis $C_{32}H_{19}N_3O_5$: Calculated: C 73.1%, H 3.6%; N 8.0%. Found: C 72.9%; H 3.6%; N 7.8%.

Molecular weight 525.5 m/e=525 (M+) (molecular weight determined by mass spectrometry)

For conversion into the pigment form, 30 g of the crude pigment obtained were charged in a grinding vessel of approximately 1 l capacity with 300 ml of acetone and 1200 g of quartzite beads, φ 2–3 mm, and milled for 12 hours on a vibrating mill. The milled material was separated from the beads through a screen, and the pigment suspension obtained was evaporated to dryness in a rotary evaporator. A deep black pigment powder was obtained in virtually quantitative yields.

2. Preparation of the Compound According to the Formula

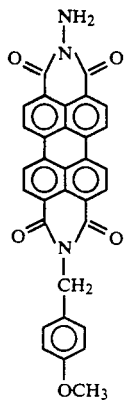

The procedure was as in Example 1, except that the same amount of the corresponding 4'-methoxybenzylimide was used instead of perylene-3,4,9,10-tetracarboxylic mono-3'-methoxybenzylimide. 15.3 g (97.7% of theory) of the corresponding black diimide were obtained.

Analysis $C_{32}H_{19}N_3O_5$: Calculated: C 73.1%; H 3.6%; N 8.0%. Found: C 73.5%; H 3.7%; N 8.1%.

Molecular weight 525.5 m/e=525 (M+)

The crude pigment was milled as described in Example 1.

3. 20.3 g of perylene-3,4,9,10-tetracarboxylic mono-N-aminoimide were reacted in 300 ml of quinoline in the presence of 5.0 g of zinc acetate with 27.4 g of 3-methoxybenzylamine at 200°–210° C. over a period of 6 hours, while distilling off the water of reaction. The black reaction product was filtered off with suction, washed with quinoline, methanol and water and dried.

Yield: 24.5 g (93.3% of theory)

The black crude pigment obtained corresponded to the product obtained according to Example 1.

4. Preparation of the Compounds According to the Formula

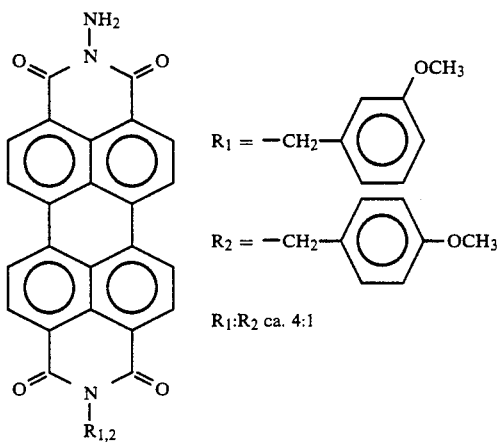

$R_1:R_2$ ca. 4:1

A mixture of 12.3 g of perylenetetracarboxylic mono-3'-methoxybenzylimide and 3.1 g of perylenetetracarboxylic mono-4'-methoxybenzylimide was introduced into a solution of 9.8 g of hydrazinium sulfate (99% pure) and 16.0 g of 50% potassium hydroxide solution in 400 ml of 60% ethanol and then reacted in an autoclave at 130°–140° C. for 5 hours. The black crystals were filtered off with suction, washed with water and dried. The yield was 15.8 g (99.8% of theory).

m/e: 525 (M+)

II) WORKING EXAMPLES a) Preparation of a 5% Full-Strength Baked Coating

A mixture of 62.5 ml of quartzite beads, φ 3 mm, 4.5 g of the pigment according to Example I.1 or I.2 and 25.5 g of a commercially available alkyd resin paint (solids content 35% by weight) were dispersed in a plastic beaker on a paint shaker for 30 minutes. 60 g of a commercially available alkyd/melamine resin paint (solids content 55.8% by weight) were then added and, after dispersing for another 5 minutes, the quartzite beads were removed through a screen. The paints were applied to white cardboard in a coating thickness of 100

μm using a "handcoater" (No. 8) and baked at 140° C. for 30 minutes.

b) Preparation of a Baked Coating Using a 1:5 White Reduction Paint 12.0 g of the two full-strength paints prepared according to a) were mixed with 10 g each of a commercially available white alkyd/melamine resin paint having a titanium dioxide content of 30% by weight. The paints thus obtained were applied, as described in a), to white cardboard using a handcoater and baked.

The diffuse reflection curves of the coatings obtained according to a) and b) were recorded. The curves are shown in the Appendix in FIGS. 1 (Example 1) and 2 (Example 2). Curve a corresponds in each case to the full-strength coating and curve b to the white reduction paint. The reflection spectra were measured in the wavelength region from 400 to 1200 nm, using a lead sulfide cell in a spectrophotometer DK 2 from Beckmann Instruments against barium sulfate as the white standard.

Compared with the pigment obtained according to Example 1 of U.S. Pat. No. 4,450,273 and milling in a vibrating mill according to the above Example I.1, the coatings of each of the white reduction paints of the pigments according to the invention had a higher color strength.

I claim:

1. A perylene-3, 4, 9, 10-tetracarboxylic diimide of the formula (I)

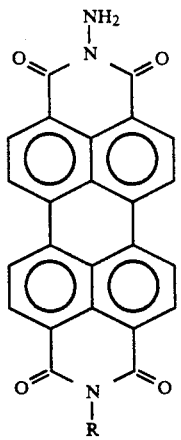

in which R is a 3- or 4-methoxybenzyl radical or mixtures of 3-methoxybenzyl and 4-methoxybenzyl radicals.

2. The perylene-3, 4, 9, 10-tetracarboxylic diimide as claimed in claim 1, wherein R is a 3-methoxybenzyl radical.

3. The perylene-3, 4, 9, 10-tetracarboxylic diimide as claimed in claim 1, wherein R is a 4-methoxybenzyl radical.

4. The perylene-3, 4, 9, 10-tetracarboxylic diimide as claimed in claim 1, wherein R is a mixture of 3-methoxybenzyl and 4-methoxybenzyl radicals.

* * * * *